United States Patent [19]
Wheeler et al.

[11] Patent Number: 5,407,695
[45] Date of Patent: Apr. 18, 1995

[54] LOW-PALMITIC, REDUCED-TRANS MARGARINES AND SHORTENINGS

[75] Inventors: Edward L. Wheeler, Fairfield; Michael Chrysam, Blairstown; Michael S. Otterburn, Randolph; Gilbert A. LeVeille, Denville, all of N.J.

[73] Assignee: Nabisco, Inc., Parisppany, N.J.

[21] Appl. No.: 850,549

[22] Filed: Mar. 13, 1992

Related U.S. Application Data

[63] Continuation-in-part of Ser. No. 804,140, Dec. 6, 1991, Pat. No. 5,258,197, which is a continuation-in-part of Ser. No. 624,056, Dec. 7, 1990, abandoned, which is a continuation-in-part of Ser. No. 410,161, Sep. 20, 1989, abandoned, and a continuation-in-part of Ser. No. 665,629, Mar. 6, 1991, abandoned.

[51] Int. Cl.$^6$ ............................................. A23D 7/00
[52] U.S. Cl. .................................. 426/603; 426/607; 426/804
[58] Field of Search ............... 426/603, 607, 804, 530, 426/581

[56] References Cited

U.S. PATENT DOCUMENTS

| | | | |
|---|---|---|---|
| 2,614,937 | 10/1952 | Baur ............................. | 426/607 |
| 2,615,159 | 10/1952 | Jackson . | |
| 2,615,160 | 10/1952 | Baur . | |
| 3,617,308 | 11/1971 | Graffelman . | |
| 3,796,581 | 3/1974 | Frommhold ................... | 426/607 |
| 3,859,447 | 1/1975 | Sreenivasan . | |
| 4,217,372 | 8/1980 | Ebskamp ....................... | 426/603 |
| 4,230,737 | 10/1980 | Heider et al. . | |
| 4,316,919 | 2/1982 | Pelloso et al. . | |
| 4,366,181 | 12/1982 | Dijkshoorn .................... | 426/607 |
| 4,386,111 | 5/1983 | Van Heteren ................. | 426/603 |
| 4,390,561 | 6/1983 | Blair ............................. | 426/607 |
| 4,396,639 | 8/1983 | Bodor .......................... | 426/607 |
| 4,419,291 | 12/1983 | DeLathauwer et al. . | |
| 4,425,371 | 1/1984 | Stratmann et al. . | |
| 4,479,976 | 10/1984 | Lansbergen ................... | 426/607 |
| 4,486,457 | 12/1984 | Schijf .......................... | 426/603 |
| 4,501,764 | 2/1985 | Gercama ...................... | 426/607 |
| 4,832,975 | 5/1989 | Yang ........................... | 426/804 |
| 4,948,618 | 8/1990 | Hirokawa ..................... | 426/603 |
| 5,066,510 | 11/1991 | Ehrman ........................ | 426/804 |

FOREIGN PATENT DOCUMENTS

| | | | |
|---|---|---|---|
| 816343 | of 1959 | United Kingdom . | |
| 822730 | of 1959 | United Kingdom . | |
| 2078245 | 1/1982 | United Kingdom ............ | 426/603 |
| 91/03944 | 4/1991 | WIPO ........................... | 426/804 |

OTHER PUBLICATIONS

Feuge Food Technology 9:314–318 1955.
Baur J Amer Oil Chem Soc 31 147–151 1954.
Patton 1976 Biomedical Aspects of Lactation Pergamon Press New York pp. 77–84.
Bonanome, A. and Grundy, S. M., New Eng. Jour. Med. 318: 1244–1248 (1988).
Chrysam, M., in Bailey's Industrial Oil and Fat Products, vol. 3, Wiley-Interscience, 1985 pp. 62 to 63.
Gottenbos, J. J., Chapter 8 in Beare–Rogers, J., ed., Dietary Fat Requirements in Health and and Development, A.O.C.S. 1988, p. 109.
Keys, A., et al., Metabolism 14: 766–786 (1965).
List, G. R., et al., J. Amer. Oil Chem. Soc. 54: 408–413 (1977).
Mead, J., et al., Lipids, Plenum, New York, 1986, p. 459.
Mensink, R. P. and Katan, M. B., New Eng. Jour. Med. 323: 439–445 (1990).
US Dept. of Health, Education & Welfare, Guide for the Care and Use of Laboratory Animals, National Institute of Health Bulletin No. 78.23, pp. 11 to 17.

*Primary Examiner*—Carolyn Paden

[57] ABSTRACT

Margarines and shortenings are improved by employing a blend of 75 to 25% of an edible oil as a liquid oil component, and, as a hardstock component, 25 to 75% of a substantially fully hydrogenated oil bearing $C_{16}$ to $C_{24}$ acid residues, wherein at least about 15% of the $C_{16}$ acid residues in the hydrogenated oil are replaced by the short acids acetic acid, propionic acid, butyric acid or a mixture of any of these acids. The levels of transunsaturated fatty acids and palmitic acid are reduced, and the products also have reduced caloric densities.

19 Claims, No Drawings

LOW-PALMITIC, REDUCED-TRANS MARGARINES AND SHORTENINGS

RELATED U.S. APPLICATION DATA

This is a continuation-in-part of U.S. application Ser. No. 07/804,140, filed Dec. 6, 1991, now U.S. Pat. No. 5,258,197, which was a continuation-in-part of Ser. No. 07/624,056 filed on Dec. 7, 1990, now abandoned, which was a continuation-in-part of 07/410,161 filed Sep. 20, 1989, now abandoned, and a CIP of U.S. application Ser. No. 07/665,629, filed Mar. 6, 1991, now abandoned.

TECHNICAL FIELD

This invention relates to new margarine products and solid fats for use in these margarines and as shortenings which significantly reduce levels of both transunsaturated and palmitic fatty acids but yet provide acceptable physical properties and decreased caloric density.

The quality of a margarine is directly related to its fat content, including the presence of a hardstock which gives it a solid, but spreadable, texture—like butter.

The achievement of good texture has relied upon partially hydrogenating fats and employing those fats which do not cause excessive graining and which are not excessively hard after hydrogenation. Thus, margarines available commercially tend to have both trans unsaturation and significant levels of palmitic acid. Both of these have been criticized for possible health risks when consumed in large quantities over time.

Margarine, butter, and other fat-based spreads typically contain as much as 80% fat by weight. Shortenings are essentially all fat. For weight-watchers, this is a problem because dietary fat is the most concentrated source of energy of all the nutrients, supplying 9 kcal/gram, about double that contributed by either carbohydrate or protein. The amount of fat in the American diet has increased in the last 60 years by about 25% (Mead, J., et al. Lipids, Plenum, New York, 1986, page 459), so that fats now provide approximately 40% (or more) of the daily caloric intake.

A number of national advisory committees on nutrition have recommended that the total amount of fat in the diet be reduced significantly (Gottenbos, J. J., chapter 8 in Beare-Rogers, J., ed., *Dietary Fat Requirements in Health and Development*, A.O.C.S. 1988, page 109). For those individuals who do not voluntarily reduce their fat intakes, it would be beneficial to provide margarines and like products which are both good tasting and compatible with the reasonable nutritional goals of consumers. It would be an advantage in this regard to reduce both trans unsaturation and palmitic acid.

BACKGROUND ART

Margarine and shortenings prepared from vegetable oils are perceived by many as more healthy than butter and lard. This perception is justified because animal fats typically contain cholesterol and have higher levels of palmitic acid than common margarine oils. To date, however, it has not been possible to realize the full promise of the health benefits of margarine and related fatty products.

Some dietary fats present in butter and useful in making quality margarine, notably those high in lauric acid (12:0), myristic acid (14:0), or palmitic acid (16:0), have been reported to increase plasma cholesterol concentrations, while fats high in stearic acid do not (Bonanome, A., and Grundy, S. M., New Eng. *Jour. Med.* 318: 1244–1248 (1988)). In most diets, palmitic acid dominates this group of saturated fats (Keys, A., et al., *Metabolism* 14: 766–786 (1965)), so a decrease in dietary palmitic acid would be beneficial.

The plastic properties of margarine fats are improved through hydrogenation, but the resulting fats have been criticized as less healthy than vegetable oils with high cis unsaturation. Most natural vegetable fats and oils contain only cis double bonds, but partial hydrogenation results in the formation of trans fatty acid substituents. Recent studies have investigated the effect of trans fatty acids on raising low-density lipoprotein serum cholesterol levels and lowering high density lipoprotein serum cholesterol levels in adults fed fats having these acids (Mensink, R. P., and Katan, M. B., New Eng. *Jour. Med.* 323: 439–445 (1990)).

Margarines formulated with oils containing low levels of palmitic acid, e.g., safflower oil, canola oil, and sunflower oil, have been suggested, but these have a tendency to become grainy during storage because the polymorphism of the fat crystals tend to stable beta forms that have a coarse, sandy texture (Chrysam, M., in *Bailey's Industrial Oil and Fat Products*, vol. 3, Wiley-Interscience, 1985, pages 62 to 63). In severe cases, the crystal transformation may result in exudation of the liquid oil from the product and partial coalescence of the aqueous phase, which increases the microbiological susceptibility (ibid.). Randomization of the hard component (U.S. Pat. No. 4,316,919 to Pelloso and Kogan) or interesterification of the hard with part of the liquid portion (U.S. Pat. No. 4,230,737 to Heider and Wieske) have also been suggested to prevent texture problems, but these products have a partially hydrogenated component and contain trans fatty acids.

Various research efforts have been directed to the development of edible fats that mimic the physical and organoleptic properties of partially-hydrogenated fats but have diminished or zero trans acid contents. For example, interesterified fat products have been prepared using fully-hydrogenated hardstocks (U.S. Pat. No. 3,617,308 to Graffelman), including those having no trans isomers (List, G. R., et al., *J. Amer. Oil Chem. Soc.* 54: 408–413 (1977)). Fat blends using a stearin fraction instead of hydrogenated and interesterified fats have been disclosed for producing margarines (U.S. Pat. No. 4,366,181 to Dijkshoorn, et al.). Low trans fat products have also been prepared by fractionating an interesterified mixture of liquid and completely hydrogenated oil (U.S. Pat. No. 4,425,371 to Stratmann, et al.). However, these products are formulated with palmitic acid.

Another approach to low trans products makes use of directed interesterification to prepare fats from liquid oil without the aid of hydrogenation. For example, directed interesterification of sunflower and safflower oils at low temperatures in an aprotic solvent (U.S. Pat. No. 3,859,447 to Sreenivasan) or of corn oil with temperature cycling in the absence of solvent (U.S. Pat. No. 4,419,291 to Lathauwer, et al.) has been disclosed. However, using most oils, the technique yields a plastic product having limited functionality.

It would be desirable to have margarines and solid shortenings that are low in palmitic acid, have low levels of or no trans fatty acids, and have good functional and organoleptic properties.

DISCLOSURE OF THE INVENTION

It is an object of the present invention to provide new margarine products and fats suitable for making these products and for use as solid shortening.

It is a principal object of the invention to provide margarines and solid shortenings that are low in palmitic acid and low in or free of trans fatty acids.

It is a further object of this invention to provide margarines and solid shortenings having excellent organoleptic properties and functional characteristics useful in a variety of products.

It is a further object of the invention to provide margarines and solid shortenings that are low in calories.

It is a further and more specific object of the invention to provide stick and tub margarines, shortening products and fat blends useful in preparing them which are improved through the reduction in trans unsaturation, palmitic fatty acids and caloric density.

These and other objects are achieved by the present invention which provides margarine products and solid, plastic fats for use in preparing the margarine products and for use as shortenings. The invention also provides methods for preparing these products.

The margarine products will comprise an aqueous phase and a solid plastic fat phase comprising a blend of 75 to 20% by weight of a liquid edible oil component, and, as a hardstock component, 25 to 80% by weight of a substantially fully-hydrogenated oil bearing $C_{16}$ to $C_{24}$ acid residues, and at least about 30 mole % and up to 67 mole % of one or more short chain acid residues selected from the group consisting of the residues of acetic acid, propionic acid, butyric acid and mixtures of these acids. The substitution of $C_{16}$ (palmitic) acid residues in the hardstock with short chain acid residues, reduces the palmitic acid to more acceptable levels.

Preferred blends comprise at least about 50 weight % of the hardstock component and less than about 50 weight % of the liquid oil component, and the more preferred hardstock components will contain from about 40 to about 65 mole % of the short chain acids. Preferred long residues have 18 or more carbons. The more preferred hardstock components will contain less than 10% by weight, most preferably less than 5%, palmitic acid residues and preferably less than 1%, most preferably less than 0.5% $C_6$ to $C_{14}$ fatty acid residues.

The solid plastic fats which provide the improved margarines and shortenings of the invention thus contain a blend of liquid edible oils and a hard stock wherein trans unsaturated fatty acids are reduced or eliminated and significant amounts of palmitic acid are replaced with short chain acids. The products of the invention contain larger amounts of hardstock than is found in typical plastic fat products. It is an advantage of the invention that trans unsaturation can be virtually eliminated and that the level of palmitic acid can be significantly reduced as the amount of hardstock is increased.

The margarine products will include an aqueous phase and the solid, plastic fat defined above as a fat phase. They will employ minor ingredients such as color, flavor, preservatives, vitamins and the like as known to the art. In addition to full-fat margarines of the stick (hard) and tub (soft) type, low-fat spreads, i.e. margarine substitutes with less than 80 weight % fat, are also contemplated. While these spreads do not meet the terms of the federal regulation defining margarine, they are perceived as margarines and the term margarine is employed in its nontechnical sense to include all butter-flavored full-fat and low-fat spreads. The low-fat spreads can be oil-in-water emulsions, if desired, although most such products and full-fat margarines are of the water-in-oil type. The solid shortening fats of the invention are essentially equivalent to the margarine fats, with or without additional emulsifiers and with or without an aqueous phase. The amount and composition of the hardstock(s) is adjusted to give a plastic range suitable for the intended use.

In the process of preparing margarines and shortenings of this invention, a hardstock component comprising triglycerides having short ($C_2$ to $C_4$) acid residues and long ($C_{16}$ to $C_{24}$) saturated acid residues, is mixed with a liquid edible oil component to form a blend. The blend is employed as the fat phase of a margarine or as a solid shortening fat.

The hardstock component is a fully-hydrogenated oil bearing $C_{16}$ to $C_{24}$ acid residues, wherein at least about 30 mole % and up to 67 mole %, preferably at least about 40 to about 65 mole %, of the $C_{16}$ (palmitic) acid residues have been substituted by those of acetic, propionic, or butyric acid, or a mixture of these short acids. The amount of palmitic which has been substituted by the short acids is equal to the percentage (molar) of short acid residues in the component. The word substituted is employed to define the triglyceride products and does not imply that any particular method, e.g., interesterification or transesterification was necessary to prepare the product. Indeed, any chemical synthesis can be employed, whether it involves addition, deletion and/or transfer of fatty acids, on the only condition that it be effective to produce the triglycerides described. The fully hydrogenated oil can be derived by fractionation, hydrogenation, or chemical synthesis. The resulting hardstock comprises triglycerides bearing at least one long, saturated $C_{16}$ to $C_{24}$ fatty acid residue, at least one short $C_2$ to $C_4$ acid residue, and a third residue which can be either short, or long and saturated.

Denoting the aliphatic portion of the long fatty acid substituent as L and the short group as S, the useful hardstocks comprise at least one of the SSL, SLS, LLS, and LSL species described by the following formulae:

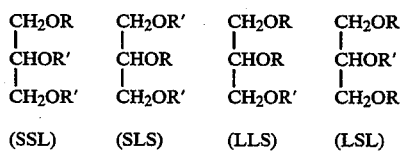

where
  each R, independently, is a long chain saturated fatty acid residue having between 16 and 24 carbons; and
  each R', independently, is a short chain acid residue having 2 to 4 carbons.

Preferred embodiments have at least two of the above species. SSL and SLS species are typically present in amounts of at least 10% of the hardstock components, but can predominate, comprising, for example, as much as 60 to 98% by weight of the component.

The hardstocks can also contain one or more triglycerides of the formulae

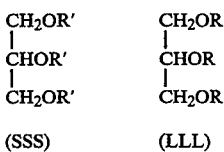

(SSS)      (LLL)

where R and R' are as defined above.

However, preferred hardstocks contain less than 2% SSS and less than 10% LLL, preferably less than 5%, most preferably less than 2% LLL and less than 1% SSS, all of these percentages being by weight. Most preferably, the SSS is less than 0.1%. In some applications, the LLL species may be removes from the hardstock or the margarine or shortening fat by fractional crystallization or distillation. Distillation has been found advantageous because it removed color bodies as well as the major portion of LLL species. A preferred technique employs high vacuum molecular distillation to maximize SSL and SLS (e.g., 90 to 98%) and minimize LLL (e.g. to less than 1%).

The hardstock component(s) are those which effectively immobilize the liquid oil component so that the margarine or solid shortening fat is dimensionally stable at 20° C. Edible oils, i.e., liquid or semi-liquid vegetable fats, on the other hand, are not dimensionally stable at 20° C., but flow under their own weight. The liquid oil can be any such oil, fraction thereof, or mixture of liquid oils, such as a member selected from the group consisting of soybean, safflower, sunflower, high oleic sunflower, sesame, peanut, corn, olive, canola, rice bran, mustard seed, cottonseed, poppyseed, rapeseed, high erucic rapeseed, marine, carrot, evening primrose, borage, meadowfoam and the like.

It is an advantage of the invention that when liquid oils such as canola oil are selected because of their low palmitic acid content, the palmitic acid content of the blend of hardstock and liquid oil can be maintained at a low level, even lower than that of the liquid oil. This is in sharp contrast to the prior art where it has typically been thought necessary to employ a hardstock, such as from cottonseed oil, having a higher palmitic acid content than the canola. When this is done according to the invention, the palmitic acid content of the hardstock can be significantly reduced. And, in the case where the oil for the liquid oil component and the hardstock come from the same source, the palmitic acid content can be reduced below that of the blend if prepared according to the prior art.

As depicted above, the hardstock component in the fats of this invention are compounds consisting of glycerol, 1,2,3-propanetriol, having the formula $(CH_2OH)_2$-$CHOH$, esterified with three molecules of the same or different acids. The acids are short $C_2$ to $C_4$ acids, or long and saturated $C_{16}$ to $C_{24}$ acids. It is possible to use one or more hardstock fats. Indeed, it is desirable for some products to employ two or three different hardstock fats with different SFI profiles.

The short acid residue, R', has no more than 4 carbons and is derived from a carboxylic acid of the formula SCOOH, where S is a short chain group such as an aliphatic having 1 to 3 carbons. As denoted herein, where R' is described as having 2, 3, or 4 carbons, compositions with R' groups having predominantly 2, 3, or 4 carbons are included. Acylation of a glycerol hydroxyl by acid SCOOH results in the attachment of short chain S to the glycerol backbone by means of an ester linkage (—O—(CO)—). Where there is more than one R' attached to a glyceride, the R' groups may be the same or different. As used herein, the term "acid residue" refers to an acyl group comprising a short chain portion, here S, and a carbonyl group, so that R'=S—(-CO)—.

Short chain S may be derived from any synthetic or natural organic acid including, acetic (ethanoic), propionic (propanoic), butyric (butanoic), and mixtures of any two or three of these. As used herein, chemical names include isomers; for example, "butyric acid" includes normal-butyric acid (butanoic) and iso-butyric (2-methylpropanoic) acid.

Mixtures of short chain fatty acids may also be used, such as, for example, those derived from specific fractions of unhydrogenated or hydrogenated fats. Harstocks employing mixtures of acetic with propionic and/or butyric are softer and melt at lower temperatures than those in which acetic is employed alone. Mixtures of butyric with propionic and/or acetic have high melting points and are harder than those in which butyric is employed alone. The mixtures can contain amounts of medium or long, unsaturated fatty acids to the extent which these can be tolerated without unduly affecting the physical properties of the margarine or shortening fat. For example, some margarine or shortening fats may contain minor amounts, such as 20 mole % or less of medium and/or long, unsaturated substituents.

The LLS/LSL species are believed important for their ability to hold the liquid oil component in a solid matrix which is formed when the blend of liquid oil and hardstock are cooled. Thus, the blends must contain sufficient amounts of the LLS/LSL species to provide a crystalline matrix capable of holding the liquid oil component in the matrix, typically at least about 25% by weight—e.g. in the range of from 30 to 98%. Where acetic acid is employed as a short acid, it is preferred to employ at least one other short acid constituent (e.g., from 10 to 90 mole %) to achieve a suitable combination of melting and oil holding properties.

The long fatty acid residue, R, has from 16 to 24, more narrowly 18 to 22, carbons. In one preferred embodiment, R has predominantly (80 weight % or higher) 18 carbons (stearic acid residues). In another embodiment R has 92 weight % or higher $C_{18}$ groups. R is an acyl group comprising an aliphatic portion and a carbonyl, and is derived from a fatty acid of the formula LCOOH, where L is a saturated aliphatic group having 15 to 23 carbons; thus, R=L—(CO)—. Acylation of a glycerol hydroxyl by acid LCOOH results in the attachment of long chain L to the glycerol backbone by means of an ester linkage (—O—(CO)—). Where there is more than one R group attached to a glycerol backbone, the R groups may be the same or different.

R may be derived from any synthetic or natural, straight or branched saturated organic acid having the requisite chain length including, but not limited to, palmitic (hexadecanoic), stearic (octadecanoic), arachidic (eicosanoic), behenic (docosanoic), lignoceric (tetracosanoic), and the like acids. R may also be derived by hydrogenating an unsaturated acid including, but not limited to, palmitoleic (9-hexadecenoic), oleic (cis-9-octadecenoic), elaidic (trans-9-octadecenoic), vaccenic (trans-11-octadecenoic), linoleic (cis, cis-9,12-octadecedienoic), linolenic (9,12,15-octadecatrienoic and 6,9,12-octadecatrienoic), eleostearic (9,11,13-octadecatrienoic), arachidonic (5,8,11,14-eicosatetraenoic), erucic (13-docosenoic), brassidic (12-docosenoic), nervonic (cis-15-tetracosenoic), 5,8,11,14,17-eicosapentanoic, 4,7,10,13,16,19-docosahexanoic and mixtures of these and other like acids. As used herein, chemical names include isomeric variations. As in the case for mixtures of short chain acids, the mixtures of long chain fatty acids can contain amounts of medium fatty acids to the extent which these can be tolerated without unduly affecting the physical properties of the margarine or shortening fat.

The various R groups are preferably mixtures of fatty acids and can be derived, for example, by hydrogenating (preferably fully, e.g. to an iodine value of less than 2) oils such as those employed as the liquid oil component. Fatty acids derived from specific fractions of processed or unprocessed oils, fats, or waxes may also be used, and are especially advantageous in some embodiments. Vegetable fats are preferred sources because they contain no cholesterol and no trans unsaturation in their natural form.

Any preparative procedure effective to produce the triglycerides bearing short and long substituents as described above, can be employed. Interesterification and transesterification procedures are preferred.

In a preferred procedure for preparing a hardstock, a feedstock vegetable oil is hydrogenated, and then reacted to replace at least 30 mole % and up to 67 mole %, preferably 40 to 65 mole %, of the palmitic residues in their complement of $C_{16}$ to $C_{24}$ saturated fatty acid residues by acetic, propionic, or butyric acid, or mixtures of these short acids. The reaction will replace not only palmitic but other long fatty acids using synthetic procedures known to the art, such as, for example, transesterifying the feedstock saturated triglycerides with esters of short chain acids of the type identified above, or interesterifying long and short chain triglycerides for such time and under such conditions that triglycerides bearing both long and short residues form. Starting materials for the preparations may be obtained commercially or isolated from natural sources. Exemplary hardstock component syntheses are given hereinafter.

The advantages of the invention can be further enhanced by employing, as at least a part of the liquid oil component, triglycerides bearing long $C_{16}$ to $C_{24}$ fatty acid residues and short $C_2$ to $C_4$ acid residues similar to the hardstock components described above, but comprising unsaturated as well as saturated long residues and having essentially no solids (e.g., less than 3%) at 70° to 100° F. Examples are given below and include the interesterification products of liquid oils such as safflower oil with acetic, propionic, butyric, or medium chain acids.

To prepare a margarine, separate oil and aqueous phases are prepared and then blended and emulsified together. The oil phase will contain, in addition to the fat blend described above, all other fat soluble components such as color, flavor and vitamins, emulsifiers, and antispatter or crystal modifying agents. Typical emulsifiers will be mono- and di-glycerides and/or lecithin. Lecithin is also a typical anti-spatter additive, and examples of coloring agents are beta-carotene, annatto, turmeric, paprika and FD&C dyes. Representative of the flavors will be lipolyzed butter oils, diacetyl, 2-octanone, butyric acid, hexanoic acid, and the like. The water phase may contain water-soluble flavors, and other water-soluble and dispersible materials such as milk or whey solids, preservatives, salt, casein, caseinates, albumins and other suitable margarine ingredients. Full-fat margarines typically employ 80% by weight fat. They can employ more, say as high as 95%, but this is unusual. Low-fat spreads employ less than 80% fat and typically contain 20 to 70 weight % of fat phase and 80 to 30 weight % aqueous phase.

The oil phase is maintained at a temperature effective to maintain all of the components of it in a liquid state prior to blending with water which is typically at a temperature effective to bring the combined mixture to a level suitable for emulsification. The emulsion may be formed using conventional in-line or tank-type mixers. After emulsification, the emulsion is pumped through a series of cooling, scraped-surface heat exchangers to promote proper crystallization during cooling. A resting or working "B" unit is typically employed before the last heat exchanger to promote crystallization.

Best Modes for Carrying Out the Invention

Stick Margarine

The low palmitic, trans-free fats of this invention are especially advantageous for their reduction of trans unsaturated and palmitic acid in stick margarine compositions. They also significantly reduce the caloric density of these products.

Preferred margarine fat hardstock components contain at least two triglyceride species bearing short and long, saturated acid residues and contain a mixture of at least one short acid substituents and at least two different long-chain substituents. The mixture preferably contains at least four triglyceride species, with more LLS/LSL species than SSL/LSL species, virtually no SSS species, and less than 5 weight % most preferably less than 2 weight %, LLL. Preferred feedstocks for the preparation of the hardstock component are high in stearic acid and include, for example, hydrogenated cottonseed, hydrogenated soybean, hydrogenated canola, hydrogenated sunflower, hydrogenated corn and hydrogenated fish oil, and blends of these.

The more preferred edible oil components contain 15% or less by weight palmitic acid; especially 10% or less by weight. Among the preferred edible liquid oil components are corn oil, canola oil, soybean oil, sunflower oil, safflower oil, and sesame oil.

The fat blend for stick margarines is prepared by blending about 25 to 80% by weight of the hardstock component with 75 to 20% by weight of the liquid edible oil component. Preferred proportions range between about 40% to 60% hardstock and 60 to 40% edible oil. One preferred embodiment contains at least about 50% hardstock component.

The oil phase components are blended to yield desirable S.F.I. values (all given in weight percent) so that the margarine may be formed and wrapped satisfactorily, maintaining the stick form without substantial oil separation at room temperature and yet rapidly melting on the tongue at below about 98° F. A preferred SFI profile will show solids contents within the following ranges:

| Temperatures | Solids (%) |
|---|---|
| 50° F. | 15 to 35 |
| 70° F. | 8 to 20 |
| 92° F. | 5 maximum |

A more preferred SFI profile will show solid contents within the following ranges:

| Temperatures | Solids (%) |
| --- | --- |
| 50° F. | 19 to 28 |
| 70° F. | 11 to 17 |
| 92° F. | 3 maximum |

Desirably, the stick margarine should remain firm at ordinary room temperature up to about 80° F., and will therefore most preferably have an SFI value at this temperature within the range of from about 6 to about 10.

The stick margarine fats of this invention have an oxidation stability which is improved compared to prior art products; good spreadability, with penetrometer readings of about 50 to 120 at 43° F.; no oil-off on storage for 4 days at 70° F.; good flavor without the addition of artificial flavors; and a smooth texture, exhibiting substantially no crystals larger than 25 u (microns) when stored at 65° F. for 10 days.

Tub Margarine

Tub margarines are similar in composition to a stick product except that the SFI solids values required for the fat phase are lower, typically calling for a 8 to 20% solids content at 50° F., and a 3 to 15% solids content at 70° F., and a maximum solids content of about 4% at 92° F. The preferred products will exhibit less than 4 ml oil-off on storage for 4 days at 70° F. and substantially no crystals larger than 25 u when stored at 65° F. for 10 days. Preferably, they exhibit penetrometer readings of from 100 to 300 at 43° F. and the SFI profile shows solids contents in the following ranges:

| Temperatures | Solids (%) |
| --- | --- |
| 50° F. | 9 to 16 |
| 70° F. | 5 to 12 |
| 92° F. | 3.5 maximum |

The margarine fats of this invention can also be advantageously employed in low-fat spread and margarine products Low, i.e., 20 to 70% by weight, fat spreads can be prepared by emulsifying the fats of this invention with an aqueous phase. Preferred fat compositions for low-fat spreads have an array of triglycerides bearing different chain length substituents. Especially advantageous fat formulations contain, for example, butyric acid short chain substituents and long chain moieties derived at least in part from fats having a variety of chain lengths, such as cottonseed oil high erucic rapeseed oil, and menhaden. Illustrative formulations are given in the Examples.

Shortenings

The shortenings of this invention can be prepared from any of the fat blends described above for either type of margarine, optionally with an emulsifier. The emulsifier will be any of those effective for the intended purpose and can be selected from the group consisting of monoglycerides, diglycerides, other lipophilic emulsifiers, hydrophilic emulsifiers, lecithin, and mixtures of any of these.

Preferred shortening fat hardstock component embodiments contain at least two triglyceride species bearing long, saturated acid residues and propionic acid, butyric acid, mixtures of acetic and propionic acid, mixtures of acetic acid and butyric acid, mixtures of propionic acid and butyric acid or mixtures of acetic acid, propionic acid, and butyric acid residues. Hardstock components having two short moieties (e.g., 40 to 90 mole %) are especially preferred for soft shortenings and hardstocks containing two longs (e.g., 40 to 90%) are sometimes preferred for shortenings requiring plasticity at higher temperatures. The hardstock components can comprise triglycerides bearing a mixture of short residues or can comprise a blend of triglycerides bearing one species of short residue with triglycerides bearing another species of short residue.

Preferred hardstock components comprise a mixture of SLS/SSL and LSL/LLS species. At least 90% of the L moieties are derived from stearic acid in preferred embodiments.

The edible liquid oil component preferably contains about 12% by weight or less palmitic acid, preferably about 5% or less. A high oleic edible oil is especially preferred, such as, for example, high oleic safflower, canola, peanut, high oleic sunflower oil or olive oil.

Typical shortening fat compositions of the invention have the following solid fat index:

| Temperatures | Solids | Preferred Solids |
| --- | --- | --- |
| 50° F. | 8–40% | 20–30% |
| 70° F. | 3–35% | 15–25% |
| 92° F. | 25% maximum | 5–20% |

The shortening fats have good hydrolytic stability, good oxidation stability using A.O.C.S. Method Cd 12-57, and good creaming characteristics.

Preferred embodiments of the shortening fats of this invention exhibit good texture and can be formulated to exhibit acceptable solid fat indices that drop at high temperatures while retaining uniform melting characteristics that resist melting at low temperatures, and that this can be accomplished without high levels of trans unsaturation and palmitic acid. Thus, an advantage of the shortening fats of this invention is that they are useful at higher temperatures than normal and can be used in hot kitchens and bakeries.

The shortening fats of this invention can be whipped and retain air well, exhibiting specific gravity decreases by as much as a factor of two. They yield surprising textures on baking and are thus especially suitable for all types of leavened baked products, both yeast raised and chemically leavened, and unleavened baked products and generally contain a flour or starch component in addition to the fat ingredient.

Another advantage of the shortenings of this invention are their excellent film forming capabilities. They are not greasy, so they can be used as coatings or coating ingredients for baked products, as well as for snack food products, including biscuits, which can be coated with fat or oil. They are also especially suitable for flakey pastries.

EXAMPLES

The following examples are presented to further illustrate and explain the present invention and should not be taken as limiting in any regard. Unless otherwise indicated, all parts and percentages are by weight, and are based on the weight at the particular stage of the processing being described.

Nuclear magnetic resonance (NMR) data reported are proton NMR data. NMR S/L ratios are mole ratios determined as the ratio of intensities of the methyl (—CH$_3$) resonances for the short and long fatty acid groups, respectively, obtained by dividing the integral areas attributable to S components by the areas attributable to the L, and have experimental errors of 5 to 10%. In a typical NMR spectrum at 300 MegaHertz or higher, the long acid methyl resonance occurs farthest upfield, at ~0.9 ppm, as a triplet. The short acid methyl resonance is structure dependent and occurs at ~2.00 ppm (acetyl groups), ~1.15 ppm (propionyl groups) and ~0.95 ppm (butyryl groups).

Differential scanning calorimetry (DSC) is used to obtain information about the melting and crystallization behavior of triglycerides. A liquid sample is cooled from about 20° C. above its melting point to about 20° C. below, held at the final temperature, and then reheated to the initial temperature. Crystallization and melting thermograms are subjected to several analyses. The melting point(s) are taken as the peak minima (endothermic transition in the down direction of the chart plotting mW per unit time versus temperature) obtained in the heating cycle, and the crystallization temperature as the peak onset in the cooling cycle. Enthalpies of phase transitions are automatically calculated in mJoules/mg of sample by choosing the two temperature points of onset of melting and 100% melted. For compound mixtures prepared from natural oils, it is useful to calculate, by integration, a solid fat index in which the percent liquid portion of the sample is calculated for any temperature. As described hereinafter, this method is employed where A.O.C.S. Methods Cd 16–81 or Cd 10–57 are not used.

Some of the examples employ supercritical fluid chromatography, SFC, as an analytical tool to determine proportions of triglyceride components. After filtering through a 0.45 micron filter, 0.1 ul of a 30 to 50 mg/ml sample is injected onto a 1×100 mm Deltabond Cyano ™ column from Keystone Scientific in a Suprex Model 200A SFC having an SFC-grade carbon dioxide mobile phase and an oven temperature of 125° C. A linear pressure gradient of 100 to 300 atmospheres is applied over a course of 20 minutes (i.e., 10 atm/min), followed by a hold at 300 atmospheres for 10 minutes. A flame ionization detector at 400° C. detects emerging mixture components run against an internal standard of methyl tetradecanoate (10 to 12 mg/mL) in methylene chloride. External standards of mono, di, and tristearin (~10 mg/mL each) are run under identical conditions. Using these peak areas, the peak areas of the sample are normalized, added together, and divided by the total to obtain percentages of the respective LSS & SLS, LLS & LSL, and LLL species in the mixtures.

To demonstrate the stability of a sample fat emulsion (oil-off), an emulsion stability stand or test tube rack is loaded with 15 ml graduated centrifuge tubes (one for each sample). The stem of a 50 mm funnel is inserted into each tube and allowed to rest on the lip of the tube. Into each funnel is placed, occluding the hole, a ¾ to 1" 40 or 60 mesh screen circle. A 25±0.01 g sample of the test emulsion is placed on the screen, and the top of the funnel is covered with Parafilm ™ film. The samples are incubated for 4 days at 70° F. and 86° F. (and sometimes 100° F.), and any liquid collected in the tube is measured.

Example 1

In this example, a low palmitic, essentially transfree stick margarine of this invention is prepared.

Hardstock Component. This component of the fat is first prepared. One molar equivalent hydrogenated canola (899 g refined, low erucic canola containing 4% palmitic acid, hydrogenated at 180° C. and 60 lbs hydrogen until the Iodine Value, IV, is ≦3) is interesterified with 2.5 molar equivalents tributyrin (obtained from Eastman Kodak, 302 g/mole) in the presence of 0.2 to 0.3% sodium methoxide by heating to ~110° C. with agitation under a vacuum for about half an hour until color develops. Phosphoric acid (~0.2 to ~0.5%, at least twice the amount of sodium methoxide) is added to stop each reaction and neutralize the mixture, followed by the addition of 0.5% activated bleaching clay (Tonsil Optimum FF), 0.5% diatomaceous earth, and 1000 ppm citric acid (dissolved in water) to decolorize and remove soaps. The reaction is continued for ½ to 1 hour at 110° C. The product is cooled to 80° C., filtered, bleached, and steam deodorized at 210° C. for 2 to 3 hours.

The product has a Mettler Drop Point (M.D.P.) determined using A.O.C.S. Method Cc 18–80 of 30.9° C. and a S.F.I. obtained using A.O.C.S. Method Cd 10–57 of 64.8% solids at 50° F., 38.7% at 70° F., 11.4% at 80° F., 4.9% at 92° F., and 5.2% at 100° F. SFC analysis shows 67% LSS/SLS species, 29% LLS/LSL species and 4% LLL species. Gas/liquid chromatography shows the following fatty acid profile, in mole %:

| $C_{4:0}$ | $C_{16:0}$ | $C_{18:0}$ | $C_{18:1}$ | $C_{18:2}$ | $C_{20:0}$ | $C_{20:1}$ | $C_{22:0}$ | $C_{24:0}$ |
|---|---|---|---|---|---|---|---|---|
| 51.2 | 2.33 | 44.30 | 0.43 | 0.10 | 1.03 | 0.03 | 0.41 | 0.18 |

Lovibond Color is assayed using a 1 inch column, and other physical characterizations listed below employ the methods denoted in the table, except for viscosity determinations.

Viscosity is determined using a Haake viscometer, Rotovisco ™ model RV12, with a M-500 measuring head consisting of a sensor system cup and a bell shaped rotor that are manually attached to a temperature vessel, then connected to a circulator and a temperature controlled waterbath. The method measures simple shear at two temperatures in the annular gap between two concentric cylinders. Continuous measurements of torque at zero up to 100 rpm are recorded on a chart from which viscosity of the liquid fat is calculated. In the practice of viscosity determinations, the sample is melted (if not already liquid) and stirred thoroughly; the temperature during melting does not exceed the melting point of the sample by more than 10° C. For each temperature, the measured value (S) from the chart is read at the point that intercepts the curve at 50 rpm and the viscosity calculated using the following equation:

$$\text{viscosity (cp)} = \frac{G \times S}{n}$$

where
G is a constant instrument factor dependent on the torque of the measuring drive unit and the geometry of the sensor system (329 with the 4.0 Sensor System NV and the equipment described herein);
S is the measured value in scale units (from the chart); and n is the test speed in rpm at the measured value.

Using these analytical techniques the following data on the hardstock component are obtained:

| Properties | Method | Results |
|---|---|---|
| Short/Long Chain Ratio | Proton NMR | 1.2 |
| Mettler Drop Point | AOCS Method Cc 18-80 | 87.6° F. |
| Smoke Point | AOCS Method Cc 9a-48 | 310° F. |
| Flash Point | AOCS Method Cc 9a-48 | 480° F. |
| Fire Point | AOCS Method Cc 9a-48 | 510° F. |
| Peroxide Value | AOCS Method Cd 8-53 | 0.20 meq/kg |
| Free Fatty Acids | AOCS Method Ca 5a-40 | 0.23% |
| Congeal Point | AOCS Method Cc 14-59 | 30.6° C. |
| Specific Gravity | AOCS Method Cc 10-25 | 0.9097 @ 60° C. |
| Refractive Index | AOCS Method Cc 7-25 | 1.4396 @ 60° C. |
| Saponification Value | AOCS Method Cd 3-25 | 287 |
| AOM Oxidative Stability | AOCS Method Cd 12-57 | 295+ hours |
| SFC @ 50° F. | AOCS Method Cd 16-81 | 78.2% |
| 70° F. | | 49.3% |
| 80° F. | | 11.8% |
| 92° F. | | 7.3% |
| 100° F. | | 7.8% |
| Viscosity @ 100° F. | Haake Viscometer | 32.9 cps |
| 150° F. | | 26.3 cps |
| Lovibond Color | AOCS Method 13b-45 | 8Red/79Yellow |
| Heat of Fusion | DSC | 121.6 mJ/mg |

Fat Blend. The margarine fat is prepared by blending 50% of the above hardstock component with 50% liquid corn oil. The blend has the appearance of partially hydrogenated corn oil.

Margarine. A stick margarine is prepared by emulsifying

| | parts |
|---|---|
| Oil Phase Ingredients | |
| Margarine Fat Blend | 80 |
| Lecithin | 0.3 |
| Mono- and Di-glycerides | 0.21 |
| Margarine Flavor and Color | 0.0062 |
| with Aqueous Phase Ingredients | |
| Water | 16.4 |
| Whey | 1.00 |
| Salt | 2.00 |
| Sodium Benzoate | 0.086 | and passing the emulsion through a cooled, scraped-surface heat exchanger in the usual process.

Palmitic Acid Content Estimates. Most margarines formulated in the United States employ soybean or corn oils (Chrysam, M. M., cited above, page 67), which have an average palmitic acid content of about 10% by weight. As noted above, the canola starting material employed in the hardstock component of the margarine fat of this example had an initial palmitic acid content of about 4%. Assuming that the remaining long chain acids in the hydrogenated oil are stearic acid, substitution of butyric acid residues for the long chain moieties in a blend comprising 67% LSS, 30% LLS and 4% LLL species results in a hardstock component having a calculated palmitic acid content of about 2.3%. Thus, substitution of butyric acid for the long chains in the hydrogenated canola decreases the palmitic acid content by about 28%.

Blending the hardstock component in a 1:1 mixture with corn oil containing 10% palmitic results in a margarine fat having a calculated palmitic acid content of about 6.4%. Therefore, the margarine of this example has about 36% less palmitic acid than a comparable soybean or corn oil margarine.

Example 2

A shortening of the invention can be prepared by mixing

| Ingredient | parts |
|---|---|
| Example 1 Hardstock Component | 50 |
| and Liquid Soybean Oil | 45 | and blending the mixture with

| | |
|---|---|
| Soybean Oil (70 IV) | 5 |
| Mono- and Diglycerides | | and then processing.

Using the palmitic acid content of the hardstock calculated in the above Example, the shortening fat has an estimated palmitic acid content of about 6.8%, which is 32% less than a comparable soybean oil shortening having a palmitic acid content of 10%.

Example 3

In this example, hardstock components are blended with liquid oils to obtain other margarine or shortening fats of this invention.

Using the preparation and purification methods of Example 1, the following low-palmitic fats are prepared by interesterifying 0.8 moles hydrogenated canola and 0.2 moles hydrogenated cottonseed oil with 2.5 (Hardstock A) and 12 (Liquid Oil B) moles of tributyrin, respectively:

| | Hardstock A | Liquid Oil B |
|---|---|---|
| M.D.P., °C. | 32.6° | 22.6° |
| S.F.I. 50° F. | 60.7% | 41.2% |
| 70° F. | 33.2% | 2.9% |
| 80° F. | 10.0% | 0% |
| 92° F. | 5.8% | 0% |
| 100° F. | 0% | 0% |
| Proton NMR | 1.2 | 1.8 |

These fats are blended with liquid (unhydrogenated) soybean oil as follows:

Fat I: 40% A + 40% B + 20% liquid soybean oil
Fat II: 60% A + 12% B + 28% liquid soybean oil
Fat III: 25% A + 55% B + 20% liquid soybean oil The fats exhibited the following properties:

| | Fat I | Fat II | Fat III |
|---|---|---|---|
| S.F.I. 50° F. | 34.7% | 31.8% | 31.2% |
| 70° F. | 7.2% | 9.9% | 3.6% |
| 80° F. | 2.8% | 4.0% | 1.7% |
| 92° F. | 2.4% | 3.3% | 1.4% |

Assuming that the canola oil has 4% and the cottonseed oil, 20% palmitic acid and that the remaining long chain moieties in both fully hydrogenated oils is stearic acid, then the 80/20 blend of canola and cottonseed oil starting material had an average palmitic acid concentration of about 7.2%. Assuming that fats A and B comprise a mixture of SSL/SLS and LLS/LSL species, mixture A contains about 55% SSL/SLS and 45%

LLS/LSL and mixture B contains about 64% SSL/SLS and 36% LLS/LSL. Thus, the blends have an estimated palmitic acid content of about 5.2% and 5.0% respectively. Therefore, replacing part of the long moieties in the canola/cottonseed starting material blend with butyric acid decreases the palmitic acid content by about 28% for mixture A and about 30% for mixture B.

Using these estimates and those of Example 1, Fat I, which employs 40% A and 40% B and 20% liquid soybean oil has a calculated palmitic acid content of about 6.1%. Fat III, which employs 25% A, 55% B and 20% liquid soybean oil, also has a calculated palmitic acid content of about 6.1%. This is 39% less palmitic acid than a comparable soybean or corn oil fat product (containing 10% palmitic acid) and 70% less than a comparable cottonseed oil fat product (containing 20% palmitic acid).

Similarly, Fat II, which employs 60% A, and 12% B and 28% liquid oil, has a calculated palmitic acid content of about 6.5%, which is 35% less than a comparable soybean or corn oil product and 68% less than a comparable cottonseed oil product.

Example 4

This example describes a low-fat spread of the invention. A hardstock component is prepared and purified as outlined in Example 1 above, except that a 1:1 reactant molar ratio of hydrogenated canola to tributyrin is employed, yielding a product having a M.D.P. of 57.9° C. and a NMR S/L of 0.8, which SFC analysis shows to contain 39% LSS/SLS, 44% LLS/LSL, and 17% LLL species.

A 60% fat, tub-type table spread may be prepared by emulsifying

| | parts |
|---|---|
| Oil Phase Ingredients | |
| A 65:35 Blend of Corn Oil:Hardstock | 59.58 |
| Lecithin | 0.20 |
| Distilled Monoglycerides from Unhydrogenated Sunflower Oil | 0.20 |
| Beta-carotene and Vitamin A Palmitate in Corn Oil | 0.005 |
| Flavor | 0.010 |
| with Aqueous Phase Ingredients | |
| Water | 37.86 |
| Salt | 2.00 |
| Potassium Sorbate | 0.10 |
| Phosphoric Acid | 0.04 | and passing the emulsion through a cooled, scraped-surface heat exchanger in the usual process.

Using the palmitic acid estimations and assumptions of Example 1 (i.e., that the hydrogenated canola starting material comprises 4% palmitic acid and 96% stearic acid), the calculated palmitic acid content of the hardstock component is 3.1%. Blending corn oil with this hardstock in a ratio of 65:35 results in a fat blend having an estimated palmitic acid content of about 7.6%. This is about 24% less than a comparable corn oil spread containing 10% palmitic acid.

Example 5

Another low-fat spread of the invention is prepared by processing 56% of Fat II described in Example 3 with 44% of an aqueous phase as set out in Example 4 above. As estimated in Example 3, Fat II has a calculated palmitic acid content of about 6.6%, so use of this fat in the spread results in an estimated palmitic acid decrease of about 34% over comparable corn or soybean oil products, and a 67% decrease over comparable cottonseed oil products.

Example 6

Another low-fat table spread of the invention is prepared in this Example. A fat is prepared by blending 39% of Example 3 hardstock component A, 60% Example 3 liquid oil component B and 1% fully hydrogenated cottonseed oil; the mixture exhibits a S.F.I. of 54.5% at 50° F., 15.9% at 70° F., 3.5% at 80° F., and 3.0% at 92° F. Seventy percent of this fat is processed with 30% of an aqueous phase as set out in Example 4 to yield the low-fat spread.

Using the calculations and assumptions of Examples 1 and 3, the spread has an estimated palmitic acid content of about 5.5%, 45% lower than a comparable soybean or corn oil product containing 10% palmitic acid, and 72% lower than a comparable cottonseed oil product containing 20% palmitic acid.

Example 7

This example illustrates other margarine or shortening fat hardstock components for preparing products of the invention, synthesized by interesterifying hydrogenated canola with different short chain acids and acid mixtures and then purifying the products as outlined in Example 1.

One mole of hydrogenated canola is interesterified with 2.5 moles tripropionin (obtained from Pfaltz & Bauer) to obtain a mixture having a M.D.P. of 34.4° C. and a NMR S/L ratio of 1.2. The S.F.I. shows 70.6% solids at 50° F., 66.1% at 70° F., 51.2% at 80° F., 7.3% at 92°, and 4.3% at 100° F.

One mole of hydrogenated canola is interesterified with 1.25 moles (Pflatz & Bauer) tripropionin and 1.25 moles triacetin to obtain a mixture having a M.D.P. of 36.8° C. and a NMR S/L ratio of 1.3. The S.F.I. shows 71.4% solids at 50° F., 69.8% at 70° F., 64.3% at 80° F., 23.0% at 92°, and 0.2% at 100° F.

One mole of hydrogenated canola is interesterified with 1.25 moles tripropionin and 1.25 moles tributyrin to obtain a mixture having a M.D.P. of 32.5° C. and a NMR S/L ratio of 1.3. The S.F.I. shows 67.7% solids at 50° F., 54.0% at 70° F., 28.1% at 80° F., 4.7% at 92°, and 4.4% at 100° F.

One mole of hydrogenated canola is interesterified with 0.5 mole triacetin, 1.0 mole tripropionin and 1.0 mole tributyrin to obtain a mixture having a M.D.P. of 35.0° C. and a NMR S/L ratio of 1.4. The S.F.I. shows 68.6% solids at 50° F., 63.2% at 70° F., 42.5% at 80° F., 4.6% at 92°, and 4.6% at 100° F.

Example 8

In this example, margarine or shortening hardstock components useful according to the invention are prepared by interesterifying fully-hydrogenated ($H_2$) high-erucic rapeseed (obtained from CSP) or fully-hydrogenated menhaden fish oil (obtained from Zapata Haynie) with tripropionin and then purifying the product as described in Example 1 above. Using different molar reactant ratios, the following hardstocks are obtained with hydrogenated high erucic rape-seed:

| H₂-High Erucic Rapeseed:Tripropionin Reactant Molar Ratio | | | |
|---|---|---|---|
| | 1:2.5 | 1:4 | 1:12 |
| M.D.P., °C. | 44.6 | 42.5 | 39.2 |
| S.F.I. 50° F. | 79.3 | 76.7 | 68.7 |
| 70° F. | 74.9 | 72.0 | 61.8 |
| 80° F. | 73.6 | 68.9 | 52.8 |
| 92° F. | 60.4 | 48.7 | 24.9 |
| 100° F. | 38.7 | 25.0 | 3.5 |
| NMR S/L | 1.2 | 1.5 | 1.9 |

Using different molar reactant ratios and hydrogenated fish oil, the following hardstock components are obtained:

| Hydrogenated Fish Oil:Tripropionin Reactant Molar Ratio | | | |
|---|---|---|---|
| | 1:2.5 | 1:4 | 1:12 |
| M.D.P., °C. | 32.7 | 31.3 | 25.9 |
| S.F.I. 50° F. | 60.5 | 55.7 | 40.6 |
| 70° F. | 41.8 | 32.4 | 13.3 |
| 80° F. | 22.2 | 12.3 | 0.2 |
| 92° F. | 3.0 | 0.0 | 0.0 |
| 100° F. | 0.3 | 0.0 | 0.0 |
| NMR S/L | 1.1 | 1.4 | 2.0 |

Example 9

This example illustrates other margarine or shortening fat hardstock components useful in the invention prepared by interesterifying various fully-hydrogenated oils with different short chain acids and acid mixtures and purifying as outlined in Example 1.

One mole of triacetin and 11 moles of tripropionin are interesterified with 0.9 mole hydrogenated canola and 0.1 mole hydrogenated high-erucic acid rapeseed oil to yield a mixture exhibiting a S.F.I. of 64.6% solids at 50° F., 53.1% at 70° F., 26.2% at 80° F., and 0% at 92° F.

Nine moles of triacetin and 3 moles of tripropionin are interesterified with 0.9 mole hydrogenated canola and 0.1 mole unhydrogenated (liquid) canola to yield a mixture having a M.D.P. of 30.9° C. and a S.F.I. of 46% solids at 50° F., 32% at 70° F., 14.7% at 80° F., 0.1% at 92° F., and 0% at 100° F.

Six moles of triacetin and 6 moles of tripropionin are interesterified with 0.9 mole hydrogenated canola and 0.1 mole liquid canola to yield a mixture having a M.D.P. of 28.2° C. and a S.F.I. of 45.3% solids at 50° F., 25.8% at 70° F., 7.5% at 80° F., and 0% at 92° F.

Five moles of triacetin and 3 moles of tripropionin are interesterified with 0.7 mole hydrogenated canola and 0.3 mole unhydrogenated (liquid) soybean oil to obtain a mixture having a M.D.P. of 26.2° C. and a S.F.I. of 36.6% solids at 50° F., 18.8% at 70° F., 0.9% at 80° F., and 0% at 92°.

Five moles of triacetin and 3 moles of tripropionin are interesterified with 0.6 mole hydrogenated canola, 0.3 mole unhydrogenated (liquid) canola, and 0.1 mole unhydrogenated (liquid) soybean oil to obtain a mixture having a M.D.P. of 23.2° C. and a S.F.I. of 27.4% solids at 50° F., 0.7% at 70° F., 0.23% at 80° F., and 0% at 92° F.

Two and a half moles of tripropionin are interesterified with 0.67 mole hydrogenated canola and 0.33 mole unhydrogenated (liquid) safflower oil to obtain a mixture having a M.D.P. of 23.4° C. and a S.F.I. of 24.1% at 50° F., 4.7% at 70° F., 1.2% at 80° F., 0.6% at 92° F., and 0% at 100° F.

One mole of hydrogenated soybean oil is interesterified with 4 moles triacetin and 0.5 mole of tripropionin to obtain a mixture having a M.D.P. of 36.3° C. and a S.F.I. of 73.2% solids at 50° F., 72.0% at 70° F., 70.3% at 80° F., 39.4% at 92° F., and 0% at 100° F.

One mole of hydrogenated cottonseed oil is interesterified with 4 moles of triacetin, 4 moles of tripropionin and 4 moles of tributyrin to obtain a mixture having a M.D.P. of 26.2° C. A NMR solids profile shows 69.9% solids at 50° F., 23.1% at 70° F., and 0% at 80° F. to 100° F.

Example 10

This example illustrates how the physical properties of the hardstock component can be varied to achieve the objectives of the invention by varying the degree of replacement of long chain residues in a hydrogenated oil with short chain residues.

Hydrogenated canola is interesterified with 0.5 to 25 molar equivalents tributyrin using the starting materials, reaction conditions, and purifications described for the preparation of the Example 1 hardstock. Using this procedure, a 1:25 molar reactant ratio of hydrogenated canola to tributyrin yields a liquid product having a M.D.P. of 18.6° C. and an NMR S/L of 2.0. Conversely, a 1:0.5 molar ratio yields a waxy product having a M.D.P. of 63.0° C. and an NMR S/L of 0.5; similarly, a 1:1 molar ratio of hydrogenated canola to tributyrin yields a product having a M.D.P. of 57.9° C. and an NMR S/L of 0.8. Using intermediate reactant ratios, the following triglyceride mixtures are obtained:

| Hydrogenated Canola:Tributyrin Reactant Molar Ratio | | | | | | | |
|---|---|---|---|---|---|---|---|
| | 1:2 | 1:2.5 | 1:3 | 1:3.5 | 1:4 | 1:4.5 | 1:12 |
| M.D.P., °C. | 35.1 | 31.8 | 30.4 | 28.7 | 27.5 | 26.6 | 22.1 |
| S.F.I. 50° F. | 68.8 | 69.5 | 66.8 | 63.6 | 63.8 | 63.4 | 54.3 |
| 70° F. | 52.3 | 53.6 | 39.6 | 33.1 | 29.8 | 24.7 | 3.8 |
| 80° F. | 24.0 | 23.7 | 8.8 | 4.7 | 3.9 | 2.1 | 0.0 |
| 92° F. | 10.0 | 9.2 | 4.3 | 3.2 | 2.3 | 1.6 | 0.0 |
| 100° F. | 9.2 | 8.8 | 4.0 | 2.6 | 0.0 | 0.0 | |
| NMR S/L | 1.2 | 1.2 | 1.3 | 1.4 | 1.5 | 1.4 | 1.8 |

Using SFC, these have the following percentages of LSS & SLS, LLS & LSL, and LLL:

| Hydrogenated Canola:Tributyrin Reactant Molar Ratio | | | | | | | |
|---|---|---|---|---|---|---|---|
| | 1:0.5 | 1:1 | 1:2 | 1:2.5 | 1:3 | 1:3.5 | 1:4 | 1:4.5 |
| % LSS/SLS | 17.0 | 39.2 | 57.2 | 67.2 | 69.4 | 73.2 | 78.1 | 80.2 |
| % LLS/LSL | 38.5 | 43.8 | 34.7 | 28.8 | 27.1 | 24.0 | 20.5 | 18.4 |
| % LLL | 44.5 | 17.1 | 8.1 | 4.0 | 3.4 | 2.7 | 1.4 | 1.4 |

Example 11

This example illustrates an anhydride synthesis of hardstock components similar to those prepared by interesterification in Example 10 above. Butyryl-stearoyl triglyceride mixtures comprising LSS, SLS, LLS, LSL, and LLL components are prepared using monostearin as a starting material.

A 3-L, 3-neck reaction flask equipped with a heating mantle, stirrer, thermometer and reflux condenser is charged with 1078 g technical grade monostearin obtained commercially from Stephan. SFC analysis of the starting material reveals 50% monoglyceride, 27% diglyceride and 23% triglyceride. The starting material is melted, 507 g butyric anhydride (~97% pure, obtained from Aldrich Chemicals) is added, and the mixture is refluxed at 175° C. for about 15 hours and then distilled to remove butyric acid. The product is purified using a falling-film still at 120° C., <1 mm Hg, and steam deodorized at <1 mm Hg, 50 mL H$_2$O, 180° C. to yield 1173 g (90.8%) of a soft beige final product having a capillary melting point of 45° C. NMR analysis shows an S/L ratio of 0.9. SFC analysis shows 56.4% SSL/SLS, 30% LSL/LLS, and 8.7% LLL (with 4.9% diglycerides).

Another mixture is prepared by charging a 3-L, 3-neck reaction flask equipped with a heating mantle, stirrer, thermometer and reflux condenser with 864 g technical grade monostearin obtained commercially from EM Chemicals (Lot # 3006101). The starting material is melted, 770 g butyric anhydride (~99% pure, obtained from Aldrich Chemicals) is added, and the mixture is refluxed at 180° C. for about 12 hours. The mixture is then distilled to remove butyric acid. The liquid product is purified using a falling-film still and steam deodorized at 0.35 mm Hg, 40 mL H$_2$O, 180° C. to yield 924 g (77%) of a brown soft solid. NMR analysis shows an S/L ratio of 1.2.

Example 12

This example illustrates the formulation of a low-fat spread of the invention using a fat comprising corn oil and a chemically prepared hardstock that is a blend of predominantly LSL/LLS propionyl-stearoyl and butyryl-stearoyl glycerides.

The hardstock component is first prepared. Propionylstearoyl glycerides are prepared by reacting a 1:1 molar ratio of distearin with propionic anhydride. A 2-L, 2-neck flask equipped with a thermometer, reflux condenser, heating mantle and stirrer is charged with 367 g distearin, which is melted prior to adding 76 g propionic anhydride. The mixture is refluxed at 125° C. for ~5 hours, left to stand overnight at room temperature, and refluxed with stirring at 80° C. for 6 hours. The mixture is distilled to yield a solid crude product that is dissolved in hexane and washed with water until neutral. Hexane is removed in vacuuo and the off-white product solid, dried. The yield is 374 g (93%).

Butyryl-stearoyl glycerides are prepared by reacting distearin with butyric anhydride (~99% pure, obtained from Aldrich). A 3-L, 3-neck flask equipped with a thermometer, reflux condenser, heating mantle and stirrer is charged with 720 g distearin, which is half melted prior to adding 204 mL butyric anhydride. The mixture is heated for ~2 ½ hours at 85° C., left to stand without heat for two days, and refluxed at 85° C. for 8 hours. The mixture is distilled twice at 1 mm Hg to yield 743 g (93%) of a hard, light brown solid.

The butyryl-stearoyl glycerides (650 g) are mixed with the propionyl-stearoyl glycerides (350 g) in a 2-L beaker and heated. The blend is steam deodorized at 180° C., 1 mm Hg, 30 mL H$_2$O to yield a product having a melting point of 37° to 39° C. and an N.M.R. S/L ratio of 0.6.

A 40% fat, tub-type table spread is be prepared emulsifying

| | parts |
|---|---|
| Oil Phase Ingredients | |
| A 75:25 Blend of Corn Oil:Hardstock | 39.38 |
| Lecithin | 0.10 |
| Distilled Monoglycerides from Unhydrogenated Sunflower Oil | 0.50 |

-continued

| | parts |
|---|---|
| Flavor | 0.010 |
| with Aqueous Phase Ingredients | |
| Water | 57.86 |
| Salt | 2.00 |
| Potassium Sorbate | 0.10 |
| Calcium Disodium EDTA | 0.006 | and passing the emulsion through a cooled, scraped-surface heat exchanger in the usual process.

The hardstock contains no palmitic acid, so, even though the fat phase contains 75% corn oil, the estimated palmitic acid content in the spread is only 7.5% (assuming a corn oil palmitic acid content of about 10%), 25% less than a comparable spread made with 100% corn oil.

Example 13

This example illustrates how it is determined that the fats of this invention or their components have a lower caloric availability than a control corn oil, using an animal feeding study.

An experimental relationship between total calories ingested and animal body weight gain is established by monitoring the body weight gain associated with consumption of a nutritionally balanced diet containing varying concentrations of a reference substance such as corn oil which has a known caloric availability. Correlations between total calories ingested and body weight gain are excellent ($r=0.99$).

Caloric availability of an unknown substance is evaluated by substituting a specific weight of the unknown substance for the reference substance and observing the body weight gain. The gain in body weight is equated to a total number of calories using the correlation previously established for the reference data. The estimated number of calories ingested are divided by the weight of unknown substance to give the apparent calories metabolized per gram for the unknown substance.

The test animals are weanling male Sprague-Dawley rats, weighing approximately 50 to 60 g prior to acclimation. After acclimation for 3 to 10 days, the test duration is 14 days. The dietary requirements are established by observing the actual feed consumption of animals provided with unlimited feed. All diets are prepared to contain 50% of the established dietary requirements plus any supplements of reference or unknown substances. In all tests so designed the test animals are maintained in very good health.

The animals are housed singly in suspended wire mesh cages which conform to the size recommendations in the Guide for the Care and Use of Laboratory Animals, Department of Health, Education and Welfare, National Institute of Health Bulletin No. 78.23, pages 11 to 17. Litter paper is changed at least three times a week. The animal room is temperature controlled, with a 12-hour light/dark cycle, and kept clean and vermin free. Water is provided ad-libitum.

There are ten animals per group. The test feeds are NIH 07 Open Formula Rodent Chow diets manufactured by Zeigler Bros., obtained as pellets or meal. Fortified diets employ 0.2% AIN-76A vitamin pre-mix obtained from Teklad. Weight gains are measured at days 0, 3, 7, 10, and 14.

The test groups are as follows:

| Group | Test Diet | Feeding Regimen |
|---|---|---|
| 1 | NIH-07 | Ad-libitum |
| 2 | NIH-07 | Pair Fed 50% of Gp. 1 |
| 3 | As Gp. 2 + 7% corn oil | Pair Fed 50% of Gp. 1 |
| 4 | As Gp. 2 + 14% corn oil | Pair Fed 50% of Gp. 1 |
| 5 | As Gp. 2 + 21% corn oil | Pair Fed 50% of Gp. 1 |

Rats were fed a diet of 21% triglyceride test substances prepared as described in the above examples as test compounds under the foregoing procedure, and their weight gains were determined. Based upon the base line corn oil control data, and the data from the test substances, the following caloric availability data (expressed as kcal/gram) were determined:

| Fat Component | kcal/g |
|---|---|
| Example 11 Butyryl-stearoyl Glycerides (S/L = 0.9) | 4.0 |
| Example 11 Butyryl-stearoyl Glycerides (S/L = 1.2) | 4.4 |
| Example 10 1:1 Hydrogenated Canola/Tributyrin | 3.6 |
| Example 10 1:2 Hydrogenated Canola/Tributyrin | 3.9 |
| Example 10 1:2.5 Hydrogenated Canola/Tributyrin | 3.9 |
| Example 10 1:3 Hydrogenated Canola/Tributyrin | 3.8 |
| Example 10 1:3.5 Hydrogenated Canola/Tributyrin | 3.8 |

Example 14

In this example, low calorie liquid margarine or shortening fat components are prepared using the interesterification and purification method of Example 1.

Tributyrin is interesterified with safflower oil obtained from Welch, Holme, and Clark. A liquid oil exhibiting a S.F.I. having no solids at 50° F. to 100° F. is obtained with safflower oil to tributyrin reactant molar ratios of 1:2.5, 1:4, and 1:12.

Similarly, tripropionin is interesterified with safflower oil to yield a liquid oil exhibiting a S.F.I. having no solids at 50° F. to 100° F. is obtained with safflower oil to tributyrin reactant molar ratios of 1:2.5, 1:4, and 1:12.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims.

We claim:

1. A stick margarine comprising:
   (a) an aqueous phase; and
   (b) a fat phase comprising a blend of
      (i) 75 to 25 weight % of an edible liquid oil component, and
      (ii) 25 to 75% of a hardstock component comprising a substantially fully hydrogenated oil bearing both $C_{16}$ to $C_{24}$ acid residues and at least about 30 mole % and up to 67 mole % of one or more short acid residues selected from the group consisting of the residues of acetic acid, propionic acid, butyric acid or a mixture of any of these acids, wherein said fat blend has an S.F.I. of 15 to 35% solids at 50° F., 8 to 20 % solids at 70° F., and a maximum of 5% solids at 92° F., good oxidation stability, penetrometer readings of about 50 to 120 at 43° F., and exhibits no oil-off on storage for 4 days at 70° F. and substantially no crystals larger than 25μ when stored at 65° F. for 10 days, said aqueous phase and said fat phase being blended together in amounts sufficient to form a stick margarine.

2. A margarine according to claim 1 wherein said hydrogenated oil is selected from the group consisting of hydrogenated canola oil, hydrogenated cottonseed oil, hydrogenated soybean oil, hydrogenated sunflower, hydrogenated corn, hydrogenated fish oil, and mixtures thereof, wherein at least 30 mole % of the $C_{16}$ to $C_{24}$ acid residues have been substituted by said short acid residues.

3. A margarine according to claim 1 wherein the hardstock component has about 40 to about 65 mole % of the palmitic acid ($C_{16}$) residues replaced by short acids.

4. A margarine according to claim 1 wherein said liquid edible oil contains 12 weight % or less by weight palmitic acid.

5. A margarine according to claim 4 wherein said liquid edible oil is selected from the group consisting of corn oil, canola oil, soybean oil, sunflower oil, peanut, safflower oil, and sesame oil and mixtures of these.

6. A margarine according to claim 1 wherein the liquid edible oil comprises a triglyceride comprising $C_{16}$ to $C_{24}$ fatty acids and at least 30 mole % and up to 67 mole % of one or more short acid residues.

7. A margarine according to claim 1 wherein the hardstock component contains less than 10% by weight palmitic acid residues and less than 1% $C_6$ to $C_{14}$ fatty acid residues.

8. A margarine according to claim 1 wherein the fat phase comprises about 40 to 60 weight % of the hardstock component and 60 to 40 weight % of the edible oil component.

9. A margarine according to claim 1 having an S.F.I. of 19 to 28% at 50° F., 11 to 17% at 70° F., and a maximum of 3% solids at 92° F.

10. A tub margarine comprising:
    (a) an aqueous phase, and
    (b) a fat phase comprising a blend of
       (i) 75 to 25% of an edible liquid oil component, and
       (ii) 25 to 75% of a hardstock component comprising a substantially fully hydrogenated oil bearing both $C_{16}$ to $C_{24}$ acid residues and at least about 30 mole % and up to 67 mole % of one or more short acid residues selected from the group consisting of the residues of acetic acid, propionic acid, butyric acid or a mixture of any of these acids,
    wherein said fat blend has an S.F.I. of 8 to 20% solids at 50° F., 3 to 15% solids at 70° F., and a maximum of 4% solids at 92° F., good oxidation stability, and exhibiting less than 4 ml oil-off on storage for 4 days at 70° F., substantially no crystals larger than 25μ when stored at 65° F. for 10 days, and a penetrometer reading of from 100 to 300 at 43° F., said aqueous phase and said fat phase being blended together in amounts sufficient to form a tub margarine.

11. A margarine according to claim 10 wherein said hydrogenated oil is selected from the group consisting of hydrogenated canola oil, hydrogenated cottonseed oil, hydrogenated sunflower oil, hydrogenated corn oil, hydrogenated soybean oil, hydrogenated fish oil, and mixtures thereof, wherein at least 30 mole % of the $C_{16}$ to $C_{24}$ acid residues have been substituted by short acid residues.

12. A margarine according to claim 10 wherein said liquid edible oil is selected from the group consisting of corn oil, canola oil, soybean oil, sunflower oil, safflower oil, and sesame oil.

13. A margarine according to claim 10 wherein the hardstock component has about 40 to about 65 mole % of the palmitic acid residues replaced by short acids.

14. A margarine according to claim 10 wherein the fat blend comprises about 40 to 60 weight % of the hardstock component and 60 to 40 weight % of the edible oil component.

15. A margarine according to claim 10 comprising from 20 to 70% of the fat blend and from 80 to 30% aqueous phase.

16. A margarine according to claim 10 wherein the liquid edible oil comprises a triglyceride comprising $C_{16}$ to $C_{24}$ fatty acids and at least 30 mole % and up to 67 mole % of one or more short acid residues.

17. A margarine according to claim 10 wherein the hardstock component contains less than 10% by weight palmitic acid residues and less than 1% $C_6$ to $C_{14}$ fatty acid residues.

18. A process for preparing a stick margarine comprising:
(a) preparing an aqueous phase;
(b) preparing a fat phase comprising a blend of
  (i) 75 to 20 weight % of an edible liquid oil component, and
  (ii) 25 to 80 weight % of a hardstock component comprising a substantially fully hydrogenated oil bearing $C_{16}$ to $C_{24}$ acid residues and at least about 30 mole % and up to 67 mole % of one or more short chain acid residues selected from the group consisting of the residues of acetic acid, propionic acid, butyric acid or a mixture of any of these acids, wherein said blend has an S.F.I. of 8 to 30% solids at 50° F., 3 to 15% solids at 70° F., and a maximum of 4% solids at 92° F., and high oxidation stability;
(c) emulsifying the aqueous and fat phases; and
(d) solidifying the emulsion to provide a stick margarine which exhibits penetrometer readings of about 50 to 120 at 43° F., and no oil-off on storage for 4 days at 70° F. and substantially no crystals larger than 25 u when stored at 65° F. for 10 days.

19. A process for preparing a tub margarine comprising:
(a) preparing an aqueous phase;
(b) preparing a fat phase comprising a blend of
  (i) 75 to 20 weight % of an edible liquid oil component, and
  (ii) 25 to 80 weight % of a hardstock component comprising a substantially fully-hydrogenated oil bearing $C_{16}$ to $C_{24}$ acid residues, and at least about 30 mole % and up to 67 mole % of one or more short chain acid residues selected from the group consisting of the residues of acetic acid, propionic acid, butyric acid or a mixture of any of these acids, wherein said blend has an S.F.I. of 8 to 20% solids at 50° F., 3 to 15% solids at 70° F., and a maximum of 4% solids at 92° F., and high oxidation stability;
(c) emulsifying the aqueous and fat phases; and
(d) solidifying the emulsion to provide a tub margarine which exhibits penetrometer readings of about 100 to 300 at 43° F., and less than 4 ml oil-off on storage for 4 days at 70° F. and substantially no crystals larger than 25 u when stored at 65° F. for 10 days.

* * * * *